(12) United States Patent
Wang et al.

(10) Patent No.: US 11,680,095 B2
(45) Date of Patent: Jun. 20, 2023

(54) MONOCLONAL ANTIBODY AGAINST NERVE GROWTH FACTOR, AND ENCODING GENE AND USE THEREOF

(71) Applicant: Akeso Biopharma, Inc., Guangdong (CN)

(72) Inventors: Zhongmin Maxwell Wang, Guangdong (CN); Baiyong Li, Guangdong (CN); Yu Xia, Guangdong (CN); Peng Zhang, Guangdong (CN)

(73) Assignee: Akeso Biopharma, Inc., Guangdong (CN)

( * ) Notice: Subject to any disclaimer, the term of this patent is extended or adjusted under 35 U.S.C. 154(b) by 164 days.

(21) Appl. No.: 17/048,442

(22) PCT Filed: Apr. 10, 2019

(86) PCT No.: PCT/CN2019/082107
§ 371 (c)(1),
(2) Date: Oct. 16, 2020

(87) PCT Pub. No.: WO2019/201133
PCT Pub. Date: Oct. 24, 2019

(65) Prior Publication Data
US 2021/0155683 A1    May 27, 2021

(30) Foreign Application Priority Data

Apr. 17, 2018 (CN) .......................... 201810344670.3
Nov. 7, 2019 (CN) .......................... 201811320006.1

(51) Int. Cl.
| | | |
|---|---|---|
| A61K 39/00 | (2006.01) | |
| A61K 39/395 | (2006.01) | |
| G01N 33/53 | (2006.01) | |
| C12P 21/06 | (2006.01) | |
| C12N 5/20 | (2006.01) | |
| C12N 15/00 | (2006.01) | |
| C07K 16/00 | (2006.01) | |
| C07K 16/46 | (2006.01) | |
| C07H 21/04 | (2006.01) | |
| C07K 16/22 | (2006.01) | |
| A61P 19/02 | (2006.01) | |
| A61P 29/00 | (2006.01) | |
| C07K 16/42 | (2006.01) | |

(52) U.S. Cl.
CPC .............. *C07K 16/22* (2013.01); *A61P 19/02* (2018.01); *A61P 29/00* (2018.01); *C07K 16/42* (2013.01); *A61K 2039/505* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,816,567 A | 3/1989 | Cabilly et al. |
| 2004/0237124 A1 | 11/2004 | Pons et al. |
| 2013/0344068 A1 | 12/2013 | Garcia-Martinez et al. |

FOREIGN PATENT DOCUMENTS

| CN | 1849138 A | 10/2006 |
| CN | 102459337 A | 5/2012 |
| CN | 102746399 A | 10/2012 |
| CN | 104910274 A | 9/2015 |
| CN | 109553683 A | 4/2019 |
| WO | WO-2009023540 A1 | 2/2009 |

OTHER PUBLICATIONS

Enomoto et al., "Anti-nerve growth factor monoclonal antibodies for the control of pain in dogs and cats", Veterinary Record 184(1):23, pp. 1-14 (2018).
Miyagi et al., "The efficacy of nerve growth factor antibody in a mouse model of neuropathic cancer pain", Experimental Animals 65(4):337-343 (2016).
Xu et al., "The anti-NGF antibody muMab 911 both prevents and reverses pain behaviour and subchondral osteoclast numbers in a rat model of osteoarthritis pain," Osteoarthritis and Cartilage 24(9):1587-1595 (2016).
Alfthan et al.,"Properties of a single-chain antibody containing different linker peptides," Protein Eng. 8(7):725-731 (1995).
Bird et al., "Single-chain antigen-binding proteins," Science 242:423 426 (1988).
Choi et al. "Recombinant chimeric OKT3 scFv IgM antibodies mediate immune suppression while reducing T cell activation in vitro," Eur. J. Immunol. 31: 94-106 (2001).
Chothia & Lesk, "Canonical structures for the hypervariable regions of immunoglobulins," J Mal. Biol. 196:901-917 (1987).

(Continued)

*Primary Examiner* — Maher M Haddad
(74) *Attorney, Agent, or Firm* — Cooley LLP; Chen Chen (57) ABSTRACT

The present invention discloses a monoclonal antibody against nerve growth factor, and an encoding gene and use thereof. The monoclonal antibody against nerve growth factor of the present invention comprises heavy chains comprising a heavy chain constant region and a heavy chain variable region, and light chains comprising a light chain constant region and a light chain variable region. The heavy chain variable region comprises three complementarity determining regions HCDR1, HCDR2 and HCDR3, and the light chain variable region comprises three complementarity determining regions LCDR1, LCDR2 and LCDR3. The monoclonal antibody against nerve growth factor of the present invention can specifically bind to nerve growth factor, and can be used to detect the presence and/or level of nerve growth factor, as well as to prepare a drug for inhibiting the nerve growth factor-dependent proliferation of TF-1 cells, and to prepare a drug for treating or preventing at least one of neuropathic pain, chronic pain, and inflammatory pain, thus having good application prospects and marketing value.

21 Claims, 4 Drawing Sheets

Specification includes a Sequence Listing.

(56) References Cited

OTHER PUBLICATIONS

Chothia et al., "Conformations of immunoglobulin hypervariable regions," Nature 342(6252):877-883 (1989).
Clark, "Antibody humanization: a case of the 'Emperor's new clothes?" Immunol. Today 21:397-402 (2000).
Holliger et al., ""Diabodies": small bivalent and bispecific antibody fragments," Proc. Natl. Acad. Sci. USA 90(14): 6444-6448 (1993).
Hu et al., "Minibody: A novel engineered anti-carcinoembryonic antigen antibody fragment (single-chain Fv-CH3) which exhibits rapid, high-level targeting of xenografts," Cancer Res. 56:3055-3061 (1996).
Huston et al., "Protein engineering of antibody binding sites: recovery of specific activity in an antidigoxin single-chain Fv analogue produced in *Escherichia coli*," Proc. Natl. Acad. Sci. USA 85:5879 5883 (1988).
Jones et al., "Replacing the complementarity-determining regions in a human antibody with those from a mouse," Nature, 321:522-525 (1986).
Kipriyanov et al., "Bispecific tandem diabody for tumor therapy with improved antigen binding and pharmacokinetics," J. Mol. Biol. 293(1):41-56 (1999).
Poljak RJ et al., "Production and structure of diabodies," Structure 2:1121 1123 (1994).
Presta, "Antibody engineering," Current Opinion in Structural Biology 2(4):593-596 (1992).
Reichmann et al., "Reshaping human antibodies for therapy," Nature, 332(6162):323-329 (1988).
Roovers, et al., "In vitro characterisation of a monovalent and bivalent form of a fully human anti Ep-CAM phage antibody," Cancer Immunol Immunotherapy 50(1):51-59 (2001).
Ward et al., "Binding activities of a repertoire of single immunoglobulin variable domains secreted from *Escherichia coli*," Nature 341:544 546 (1989).

SEQUENCE LISTING

<160> NUMBER OF SEQ ID NOS: 10

<210> SEQ ID NO 1
<211> LENGTH: 363
<212> TYPE: DNA
<213> ORGANISM: Artificial Sequence
<220> FEATURE:
<223> OTHER INFORMATION: Nucleotide sequence of the heavy chain variable
      region of monoclonal antibody H26L17 (Artificial Sequence)

<400> SEQUENCE: 1
caggtgcagc tgcaggaaag cggaccagga ctggtgaagc ctagcgagac cctgagcctg     60
acttgtaccg tgtccggatt cgatctgagc ggctacgacc tgaattggat cagacagcct    120
cccggaaagg gcctggagtg gatcggtatc gtctggggag acggcagcag cgattacaac    180
agcgccgtga agagccgcgt gacaatcagc aaggacacca gcaagaacca gttcagcctg    240
aagctgtcta gcgtgacagc cgccgataca gcagtgtact attgcgtgcg gggcggctat    300
tggtacgcca ccagctacta cttcgactat tggggccagg aacactggt gaccgtgtct    360 tct                                                                 363

<210> SEQ ID NO 2
<211> LENGTH: 121
<212> TYPE: PRT
<213> ORGANISM: Artificial Sequence
<220> FEATURE:
<223> OTHER INFORMATION: Amino acid sequence of the heavy chain variable
      region of monoclonal antibody H26L17 (Artificial Sequence)

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asp Leu Ser Gly Tyr
            20                  25                  30

Asp Leu Asn Trp Ile Arg Gln Pro Pro Gly Lys Gly Leu Glu Trp Ile
        35                  40                  45

Gly Ile Val Trp Gly Asp Gly Ser Ser Asp Tyr Asn Ser Ala Val Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser
        115                 120

<210> SEQ ID NO 3
<211> LENGTH: 321
<212> TYPE: DNA
<213> ORGANISM: Artificial Sequence
<220> FEATURE:
<223> OTHER INFORMATION: Nucleotide sequence of the light chain variable
      region of monoclonal antibody H26L17 (Artificial Sequence)

<400> SEQUENCE: 3
gatatccaga tgacccagag ccccagctct ctgtcagcca gcgtgggcga tagagtgacc     60
atcacttgca gagccagcga gagcatcagc agcaacctga attggtacca gcagaagcca    120
ggcaaggccc ccaagctgct gatctactac accagcagat ccacagcgg cgtgcctagc    180

```
agattcagcg aagcggcag cggcaccgac tttaccttca ccatcagctc tctgcagccc      240
gaggacatcg ccacctacta ttgccagcag gagcacaccc tgccctttac ctttggccag      300
ggaacaaagc tggagatcaa g                                                321
```

<210> SEQ ID NO 4
<211> LENGTH: 107
<212> TYPE: PRT
<213> ORGANISM: Artificial Sequence
<220> FEATURE:
<223> OTHER INFORMATION: Amino acid sequence of the light chain variable
      region of monoclonal antibody H26L17 (Artificial Sequence)

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Ser Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Phe
                85                  90                  95

Thr Phe Gly Gln Gly Thr Lys Leu Glu Ile Lys
            100                 105
```

<210> SEQ ID NO 5
<211> LENGTH: 8
<212> TYPE: PRT
<213> ORGANISM: Artificial Sequence
<220> FEATURE:
<223> OTHER INFORMATION: Heavy chain variable region complementarity
      determining region 1 (HCDR1)

<400> SEQUENCE: 5

```
Gly Phe Asp Leu Ser Gly Tyr Asp
1               5
```

<210> SEQ ID NO 6
<211> LENGTH: 7
<212> TYPE: PRT
<213> ORGANISM: Artificial Sequence
<220> FEATURE:
<223> OTHER INFORMATION: Heavy chain variable region complementarity
      determining region 2 (HCDR2)

<400> SEQUENCE: 6

```
Val Trp Gly Asp Gly Ser Ser
1               5
```

<210> SEQ ID NO 7
<211> LENGTH: 15
<212> TYPE: PRT
<213> ORGANISM: Artificial Sequence
<220> FEATURE:
<223> OTHER INFORMATION: Heavy chain variable region complementarity
      determining region 3 (HCDR3)

<400> SEQUENCE: 7

```
Val Arg Gly Gly Tyr Trp Tyr Ala Thr Ser Tyr Tyr Phe Asp Tyr
1               5                   10                  15
```

```
<210> SEQ ID NO 8
<211> LENGTH: 6
<212> TYPE: PRT
<213> ORGANISM: Artificial Sequence
<220> FEATURE:
<223> OTHER INFORMATION: Light chain variable region complementarity
      determining region 1 (LCDR1)

<400> SEQUENCE: 8

Glu Ser Ile Ser Ser Asn
1               5

<210> SEQ ID NO 9
<211> LENGTH: 3
<212> TYPE: PRT
<213> ORGANISM: Artificial Sequence
<220> FEATURE:
<223> OTHER INFORMATION: Light chain variable region complementarity
      determining region 2 (LCDR2)

<400> SEQUENCE: 9

Tyr Thr Ser
1

<210> SEQ ID NO 10
<211> LENGTH: 9
<212> TYPE: PRT
<213> ORGANISM: Artificial Sequence
<220> FEATURE:
<223> OTHER INFORMATION: Light chain variable region complementarity
      determining region 3 (LCDR3)

<400> SEQUENCE: 10

Gln Gln Glu His Thr Leu Pro Phe Thr
1               5
```

MONOCLONAL ANTIBODY AGAINST NERVE GROWTH FACTOR, AND ENCODING GENE AND USE THEREOF

RELATED APPLICATIONS

This application is a U.S. National Phase Application, filed under 35 U.S.C. § 371, of International Application No. PCT/CN2019/082107, filed on Apr. 10, 2019, which claims priority to, and the benefit of, Chinese Application No. 201811320006.1, filed on Nov. 7, 2018, and Chinese Application No. 201810344670.3, filed on Apr. 17, 2018. The contents of each of the aforementioned patent applications are incorporated herein by reference in their entireties

SEQUENCE LISTING

The instant application contains a Sequence Listing which has been submitted in ASCII format via EFS-Web and is hereby incorporated by reference in its entirety. Said ASCII copy, created on Oct. 16, 2020, is named "AKSO-004_SeqList.txt" and is about 6 KB in size.

TECHNICAL FIELD

The present invention belongs to the technical field of immunology and molecular biology. More specifically, the present invention relates to a monoclonal antibody against nerve growth factor, an encoding gene thereof, and use thereof in preparing detection kits and various drugs.

BACKGROUND

Nerve growth factor (NGF) is one of the earliest determined nerve growth trophic factors, and plays an important role in the occurrence, differentiation and function maintenance of biological neurons. NGF can bind to tropomyosin receptor kinase A (TrKA) with high affinity and can bind non-specifically to P75NTR receptor. More and more evidence shows that, in addition to having the biological effects of promoting the growth, development and survival of neurons, NGF is widely considered to be a mediator of persistent pain and chronic pain. For example, intravenous infusion of NGF can cause systemic pain reactions, and local injection of NGF can cause hyperalgesia and abnormal pain at the injection site. The secretion of NGF at the site of inflammation surges and lasts longer. In addition, in certain types of cancer, excessive NGF promotes the growth and infiltration of nerve fibers, thereby inducing cancer pain. It has been reported that the TrKA receptor knockout mice exhibit lack of pain, and NGF is considered to be a molecule closely related to pain. Evidence suggests that the use of NGF inhibitors can alleviate pain responses in animal models of neuropathic and chronic inflammatory pain. Neutralizing antibody against NGF can significantly alleviate pain in murine cancer pain model.

Antibody drugs, especially monoclonal antibodies, have achieved good efficacy in the treatment of various diseases. Preparing safe and effective anti-NGF monoclonal antibodies can provide a new class of analgesic drugs in the treatment of chronic pain and cancer pain different from opiates, non-steroids, etc. that are addictive or cause side effects in digestive tract. Currently, Tanezumab, developed by Pfizer Pharmaceuticals Co., Ltd., has shown good analgesic effects in preclinical and clinical studies. However, there is still a lack of other anti-NGF antibodies with higher activity.

SUMMARY OF THE INVENTION

The object of the present invention is to overcome the defects of low activity and species differences of antibodies against nerve growth factor in the prior art, and to provide a monoclonal antibody against nerve growth factor with high activity and eliminating species difference, and an encoding gene and use thereof, as well as use thereof in preparing detection kits and various drugs.

In order to achieve the above object of the invention, the present invention provides a monoclonal antibody that can specifically bind to human nerve growth factor, comprising heavy chains and light chains, the heavy chain comprises a heavy chain constant region and a heavy chain variable region, and the light chain comprises a light chain constant region and a light chain variable region.

The variable regions of the light chain and heavy chain determine the binding of the antigen; the variable region of each chain contains three hypervariable regions, called complementarity determining regions (CDRs) (the CDRs of the heavy chain (H) include HCDR1, HCDR2, HCDR3, and the CDRs of the light chain (L) include LCDR1, LCDR2, LCDR3; which were named by Kabat et al., see *Sequences of Proteins of Immunological Interest*, Fifth Edition (1991), Volumes 1-3, NIH Publication 91-3242, Bethesda Md.).

In the present invention, the heavy chain variable region comprises three complementarity determining regions HCDR1, HCDR2 and HCDR3, and the light chain variable region comprises three complementarity determining regions LCDR1, LCDR2 and LCDR3; wherein the amino acid sequence of the complementarity determining region HCDR1 is set forth in SEQ ID NO: 5; the amino acid sequence of the complementarity determining region HCDR2 is set forth in SEQ ID NO: 6; the amino acid sequence of the complementarity determining region HCDR3 is set forth in SEQ ID NO: 7; the amino acid sequence of the complementarity determining region LCDR1 is set forth in SEQ ID NO: 8; the amino acid sequence of the complementarity determining region LCDR2 is set forth in SEQ ID NO: 9; and the amino acid sequence of the complementarity determining region LCDR3 is set forth in SEQ ID NO: 10.

In the present invention, the amino acid sequences of 6 CDR regions are constructed, and specific modifications are made to improve the antigen-binding activity of antibody variable regions. To accommodate the changes in the CDR regions, the framework regions are also modified. However, it is necessary to ensure that the modifications of these framework regions are still compatible with human germline sequences. Framework modifications will also be analyzed to ensure that these changes have no effect on the binding of the CDR regions to antigens.

Through the technical means known to those skilled in the art, for example, through the website of the National Center for Biotechnology Information (NCBI), the complementarity determining regions (CDRs) of the heavy chain variable region and light chain variable region of the monoclonal antibody are analyzed, which are set forth in the above SEQ ID NOs: 5-7 and SEQ ID NOs: 8-10, respectively. In the present invention, this monoclonal antibody is named as H26L17.

As a preferred technical scheme of the monoclonal antibody against nerve growth factor of the present invention, the amino acid sequence of the heavy chain variable region is set forth in SEQ ID NO: 2; the amino acid sequence of the light chain variable region is set forth in SEQ ID NO: 4.

As a further preferred technical scheme of the monoclonal antibody against nerve growth factor of the present invention, the nucleotide sequence encoding the heavy chain variable region is set forth in SEQ ID NO: 1; the nucleotide sequence encoding the light chain variable region is set forth in SEQ ID NO: 3.

In one embodiment of the monoclonal antibody against nerve growth factor of the present invention, the monoclonal antibody against nerve growth factor is selected from a Fab, a Fab', an F(ab')2, an Fd, an Fv, a dAb, a complementarity determining region fragment, a single chain antibody (e.g., scFv), a humanized antibody, a chimeric antibody, and a diabody.

In one embodiment of the monoclonal antibody against nerve growth factor of the present invention, the monoclonal antibody against nerve growth factor binds to NGF protein with an $EC_{50}$ of less than 100 nM (e.g., less than about 10 nM, 1 nM, 0.9 nM, 0.8 nM, 0.7 nM, 0.6 nM, 0.5 nM, 0.4 nM, 0.3 nM, 0.2 nM, 0.1 nM, or less). Wherein, $EC_{50}$ can be measured by ELISA sandwich method.

In one embodiment of the monoclonal antibody against nerve growth factor of the present invention, the monoclonal antibody against nerve growth factor comprises a non-CDR region, and the non-CDR region is from a species other than murine, for example, from a human antibody.

In order to achieve the above object of the invention, the present invention also provides a gene encoding the above monoclonal antibody against nerve growth factor.

In order to achieve the above object of the invention, the present invention also provides a vector comprising the nucleotide sequence of the heavy chain variable region and/or the nucleotide sequence of the light chain variable region.

In order to achieve the above object of the invention, the present invention also provides a host cell comprising the nucleotide sequence of the heavy chain variable region and/or the nucleotide sequence of the light chain variable region; or a vector comprising the nucleotide sequence of the heavy chain variable region and/or the nucleotide sequence of the light chain variable region.

In order to achieve the above object of the invention, the present invention also provides a method for preparing the monoclonal antibody against nerve growth factor, which includes culturing the host cell of the present invention under suitable conditions, and isolating the monoclonal antibody against nerve growth factor from the cell culture.

The present invention also provides a monoclonal antibody conjugate, comprising the monoclonal antibody against nerve growth factor and a conjugated portion conjugated thereto, wherein the conjugated portion is a detectable label. Preferably, the conjugated portion is a radioisotope, a luminescent substance, a colored substance or an enzyme.

The present invention also provides a kit, comprising the monoclonal antibody against nerve growth factor and/or the monoclonal antibody conjugate.

As a preferred technical scheme of the kit of the present invention, the kit further comprises a secondary antibody which specifically recognizes the monoclonal antibody against nerve growth factor; in addition, the secondary antibody further comprises a detectable label, such as a radioisotope, a luminescent substance, a colored substance, or an enzyme.

The present invention also provides use of the monoclonal antibody against nerve growth factor and/or the monoclonal antibody conjugate in the kit that can detect the presence and/or level of nerve growth factor. The kit is used to detect the presence or level of NGF in a sample.

The present invention also provides a drug comprising the monoclonal antibody against nerve growth factor and/or the monoclonal antibody conjugate; optionally, it further comprises pharmaceutically acceptable carriers and/or excipients.

The above drug specifically binds to nerve growth factor and can be used to inhibit nerve growth factor-mediated biological effects, such as the proliferation of TF-1 cells; and/or to treat or prevent neuropathic pain, chronic pain, and inflammatory pain.

The present invention, through in vivo experiments, has found that the monoclonal antibody against nerve growth factor of the present invention can improve the change of walking behavior of the affected limb and the condition of weight loss of the animal in the knee arthritis pain model of Lenti-IL-1β-NIH/3T3 mice.

In the present invention, unless otherwise defined, the scientific and technical terms used herein have the meanings generally understood by those skilled in the art. In addition, the laboratory operations of cell culture, molecular genetics, nucleic acid chemistry and immunology used in the present invention are the routine operations widely used in the corresponding fields. Meanwhile, in order to better understand the present invention, the definitions and explanations of the relevant terms are provided below.

As used in the present invention, the term "antibody" refers to an immunoglobulin molecule that generally consists of two pairs of polypeptide chains (each pair with one "light" (L) chain and one "heavy" (H) chain). Antibody light chains are classified as κ and λ light chains. Heavy chains are classified as μ, δ, γ, α, or ε. And isotypes of antibodies are defined as IgM, IgD, IgG, IgA, and IgE, respectively. In light chains and heavy chains, the variable region and constant region are linked by a "J" region of about 12 or more amino acids, and the heavy chain also comprises a "D" region of about 3 or more amino acids. Each heavy chain consists of a heavy chain variable region ($V_H$) and a heavy chain constant region ($C_H$). The heavy chain constant region consists of three domains ($C_H1$, $C_H2$ and $C_H3$). Each light chain consists of a light chain variable region ($V_L$) and a light chain constant region ($C_L$). The light chain constant region consists of one domain $C_L$. The constant region of the antibody can mediate the binding of immunoglobulins to host tissues or factors, including the binding of various cells (e.g., effector cells) of the immune system and the first component (C1q) of classical complement system. The $V_H$ and $V_L$ regions can be further subdivided into highly variable regions (called complementarity determining regions (CDRs)), and between which conservative regions called framework regions (FRs) are distributed. Each $V_H$ and $V_L$ consists of 3 CDRs and 4 FRs arranged from amino terminal to carboxyl terminal in the following order: FR1, CDR1, FR2, CDR2, FR3, CDR3, FR4. The variable regions ($V_H$ and $V_L$) of each heavy chain/light chain pair form antibody binding sites, respectively. The assignment of amino acids to each region or domain follows the definition of Kabat *Sequences of Proteins of Immunological Interest* (National Institutes of Health, Bethesda, Md. (1987 and 1991)), or Chothia & Lesk (1987) *J. Mol. Biol.* 196:901-917; Chothia et al. (1989) Nature 342:878-883. The term "antibody" is not limited by any specific method for producing antibody. For example, the antibody includes, in particular, a recombinant antibody, a monoclonal antibody and a polyclonal antibody. Antibodies can be different isotypes of antibodies, such as antibodies IgG (e.g., subtype IgG1, IgG2, IgG3 or IgG4), IgA1, IgA2, IgD, IgE or IgM.

As used in the present invention, the term "antigen binding fragment" of an antibody refers to the polypeptide comprising the fragment of a full-length antibody, which maintains the ability to specifically bind to the same antigen to which the full-length antibody binds, and/or competing with the full-length antibody for the specific binding to antigen, which is also known as the "antigen binding portion". See generally, Fundamental Immunology, Ch. 7 (Paul, W., ed., 2nd edition, Raven Press, N.Y. (1989), which is incorporated herein by reference in its entirety for all purposes. Antigen binding fragments of the antibody can be produced by recombinant DNA technology or by enzymatic or chemical cleavage of intact antibodies. In some cases, the antigen binding fragment includes a Fab, a Fab', an F (ab')$_2$, an Fd, an Fv, a dAb, a complementarity determining region (CDR) fragment, a single chain antibody fragment (e.g., scFv), a chimeric antibody, a diabody and a polypeptide comprising at least a portion of the antibody sufficient to impart specific antigen binding ability to a polypeptide.

As used in the present invention, the term "Fd fragment" refers to an antibody fragment consisting of $V_H$ and $C_H1$ domains; the term "Fv fragment" refers to an antibody fragment consisting of the $V_L$ and $V_H$ domains of a single arm of an antibody; the term "dAb fragment" refers to an antibody fragment consisting of a $V_H$ domain (Ward et al., Nature 341:544-546 (1989)); the term "Fab fragment" refers to an antibody fragment consisting of $V_L$, $V_H$, $C_L$, and $C_H1$ domains; and the term "F (ab')$_2$ fragment" refers to an antibody fragment comprising two Fab fragments linked by the disulfide bridge on a hinge region.

In some cases, the antigen binding fragment of the antibody is a single chain antibody (e.g., scFv) in which the $V_L$ and $V_H$ domains are paired to form a monovalent molecule via a linker that enables them to produce a single polypeptide chain (see, e.g., Bird et al., *Science* 242:423-426 (1988) and Huston et al., *Proc. Nat. Acad. Sci. USA* 85:5879-5883 (1988)). Such scFv molecules have a general structure: NH$_2$-V$_L$-linker-V$_H$—COOH or NH$_2$-V$_H$-linker-V$_L$-COOH. An appropriate prior art linker consists of a repeating GGGGS amino acid sequence or a variant thereof. For example, a linker having the amino acid sequence (GGGGS)$_4$ can be used, but variants thereof can also be used (Holliger et al. (1993), *Proc. Natl. Acad. Sci. USA* 90: 6444-6448). Other linkers that can be used in the present invention are described by Alfthan et al. (1995), *Protein Eng.* 8:725-731, Choi et al. (2001), *Eur. J. Immunol.* 31: 94-106, Hu et al. (1996), *Cancer Res.* 56:3055-3061, Kipriyanov et al. (1999), *J. Mol. Biol.* 293:41-56 and Roovers et al. (2001), *Cancer Immunol.*

In some cases, the antigen binding fragment of the antibody is a diabody, that is, a bivalent antibody, in which the $V_H$ and $V_L$ domains are expressed on a single polypeptide chain.

However, the linker used is too short to allow the pairing of the two domains on one chain, thereby the domains are forced to pair with the complementary domains on another chain and two antigen binding sites are generated (see, e.g., Holliger P. et al., *Proc. Nat. Acad. Sci. USA* 90:6444-6448 (1993), and Poljak R. J. et al., *Structure* 2: 1121-1123 (1994)).

Antigen binding fragments of antibodies can be obtained from given antibodies by using conventional techniques known to those skilled in the art (e.g., recombinant DNA technology or enzymatic or chemical cleavage), and the antigen binding fragments of the antibodies are screened for specificity in the same way as for intact antibodies.

In the present invention, unless otherwise clearly defined in the context, when referring to the term "antibody", it includes not only intact antibodies but also antigen binding fragments of antibodies.

As used in the present invention, the terms "McAb" and "monoclonal antibody" refer to an antibody or a fragment of an antibody that is derived from a group of highly homologous antibodies, i.e., from a group of identical antibody molecules, except for natural mutations that may occur spontaneously. The monoclonal antibody has a high specificity for a single epitope on an antigen. The polyclonal antibody, relative to the monoclonal antibody, generally comprises at least two or more different antibodies which generally recognize different epitopes on an antigen. Monoclonal antibodies can generally be obtained by hybridoma technology first reported by Kohler et al. (Nature, 256:495, 1975), but can also be obtained by recombinant DNA technology (for example, see U.S. Pat. No. 4,816,567).

As used in the present invention, the term "humanized antibody" refers to an antibody or antibody fragment obtained when all or a part of CDR regions of a human immunoglobulin (receptor antibody) are replaced by the CDR regions of a non-human antibody (donor antibody), wherein the donor antibody may be a non-human (e.g., mouse, rat or rabbit) antibody having expected specificity, affinity or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, for example, Jones et al., Nature, 321:522 525 (1986); Reichmann et al., Nature, 332:323 329 (1988); Presta, Curr. Op Struct. Biol., 2:593 596 (1992); and Clark, Immunol. Today 21:397 402 (2000).

As used in the present invention, the term "epitope" refers to a site on the antigen that an immunoglobulin or antibody specifically binds to. "Epitope" is also called in the art as an "antigenic determinant". The epitope or antigenic determinant generally consists of chemically active surface groups of a molecule such as amino acids or carbohydrates or sugar side chains, and usually has specific three-dimensional structural characteristics and specific charge characteristics. For example, the epitope generally includes at least 3, 4, 5, 6, 7, 8, 9, 10, 11, 12, 13, 14, or 15 consecutive or non-consecutive amino acids in a unique spatial conformation, which can be "linear" or "conformational". See, for example, Epitope Mapping Protocols in Methods in Molecular Biology, Vol. 66, G. E. Morris, Ed. (1996). In a linear epitope, all interacting points between a protein and an interacting molecule (e.g., an antibody) exist linearly along the primary amino acid sequence of the protein. In a conformational epitope, the interacting points exist across the protein amino acid residues that are separated from each other.

As used in the present invention, the term "isolated" refers to "obtained by artificial means from natural state". If a certain "isolated" substance or component appears in nature, it may be due to the change in its natural environment, or it is isolated from the natural environment, or both. For example, a certain non-isolated polynucleotide or polypeptide naturally exists in a certain living animal, and the same polynucleotide or polypeptide with a high purity isolated from such a natural state is called an isolated polynucleotide or polypeptide. The term "isolated" does not exclude the existence of artificial or synthetic substances or other impurities that do not affect the activity of the substance.

As used in the present invention, the term "E. coli expression system" refers to an expression system consisting of E. coli (strain) and a vector, wherein the E. coli (strain) is derived from a commercially available strain, such as but not limited to GI698, ER2566, BL21 (DE3), B834 (DE3), and BLR (DE3).

As used in the present invention, the term "vector" refers to a nucleic acid vehicle into which a polynucleotide can be inserted. When the vector allows for the expression of the protein encoded by the inserted polynucleotide, the vector is called an expression vector. The vector can be introduced into a host cell by transformation, transduction, or transfection so that the genetic substance elements carried by the vector can be expressed in the host cell. Vectors are well known to those skilled in the art, including, but not limited to: plasmids; phagemids; cosmids; artificial chromosomes, such as yeast artificial chromosomes (YAC), bacterial artificial chromosomes (BAC) or P1-derived artificial chromosomes (PAC); phages such as lambda phages or M13 phages, and animal viruses, etc. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, and papovaviruses (such as SV40). A vector can contain a variety of elements that control expression, including, but not limited to, promoter sequences, transcription initiation sequences, enhancer sequences, selection elements, and reporter genes. In addition, the vector may further contain a replication initiation site.

As used in the present invention, the term "host cell" refers to cells that can be used to introduce vectors, including, but not limited to, prokaryotic cells such as E. coli or Bacillus subtilis, fungal cells such as yeast cells or aspergillus, insect cells such as S2 drosophila cells or Sf9, or animal cells such as fibroblast, CHO cells, COS cells, NSO cells, HeLa cells, BHK cells, HEK 293 cells, or human cells.

As used in the present invention, the term "specifically bind" refers to a non-random binding reaction between two molecules, such as a reaction between an antibody and an antigen it targets. In some embodiments, an antibody that specifically binds to an antigen (or an antibody that is specific for an antigen) refers to that the antibody binds to the antigen with an affinity ($K_D$) of less than about $10^{-5}$ M, such as less than about $10^{-6}$ M, $10^{-7}$ M, $10^{-8}$ M, $10^{-9}$ M, $10^{-10}$ M, or less.

As used in the present invention, the term "$K_D$" refers to a dissociation equilibrium constant for a specific antibody-antigen interaction, which is used to describe the binding affinity between the antibody and the antigen. The smaller the equilibrium dissociation constant, the tighter the antibody-antigen binding, and the higher the affinity between the antibody and the antigen. Generally, antibodies bind to antigens (e.g., L1 protein) with a dissociation equilibrium constant ($K_D$) of less than about $10^{-5}$ M, such as less than about $10^{-6}$ M, $10^{-7}$ M, $10^{-8}$ M, $10^{-9}$ M, $10^{-10}$ M, or less, for example, as determined in a BIACORE instrument using surface plasmon resonance (SPR).

As used in the present invention, the terms "monoclonal antibody" and "McAb" have the same meaning and can be used interchangeably; the terms "polyclonal antibody" and "PcAb" have the same meaning and can be used interchangeably; the terms "polypeptide" and "protein" have the same meaning and can be used interchangeably. And in the present invention, amino acids are generally represented by single-letter or three-letter abbreviations known in the art. For example, alanine can be represented by A or Ala.

As used in the present invention, the term "effective amount" refers to an amount sufficient to obtain or at least partially obtain a desired effect. For example, a prophylactically effective amount refers to an amount sufficient to prevent, stop, or delay the onset of diseases; a therapeutically effective amount refers to an amount sufficient to cure or at least partially stop a disease and complications thereof in patients suffering from the disease. It is well within the ability of those skilled in the art to determine such an effective amount. For example, the amount effective for therapeutic use will depend on the severity of the disease to be treated, the overall state of the immune system of the patient, the general condition of the patient such as age, weight and sex, the manner of drug administration, and other treatments administered concurrently, etc.

Compared with the prior art, the present invention has the following advantages:

The monoclonal antibody against nerve growth factor of the present invention can specifically bind to nerve growth factor and has the advantages of high activity and the like, and can be used to detect the presence and/or level of nerve growth factor, as well as to prepare a drug for antagonizing nerve growth factor, and to prepare a drug for treating or preventing neuropathic pain, chronic pain, and inflammatory pain, thus having good application prospects and market value.

DETAILED DESCRIPTION

The embodiments of the present invention will be described in detail below with reference to the examples.

Those skilled in the art will understand that the following examples are only used to illustrate the present invention, and should not be regarded as limiting the scope of the present invention. The cases without the specific descriptions of techniques or conditions were carried out according to the technologies or conditions described in the literature in the art (e.g., see, Guide to Molecular Cloning Experiments, authored by J. Sambrook et al., and translated by Huang Peitang et al., third edition, Science Press) or according to the product manual. Reagents or instruments used are commercially available conventional products if the manufacturers thereof are not specified.

In the following examples of the present invention, C57BL/6 mice used were purchased from Guangdong Medical Experimental Animal Center.

The positive control antibody Tanezumab used was Pfizer antibody Tanezumab (David L. Shelton. Methods for treating bone cancer by administering a Nerve Growth Factor antagonist antibody. USA, 20110243961A1. 2011-06-06).

Example 1. Design, Expression and Purification of H26L17 Heavy Chain and Light Chain Sequences 1. Design of Antibody In order to generate anti-human NGF antibody H26L17, the inventors creatively designed a series of antibody sequences based on the NGF protein sequence and three-dimensional crystal structure thereof, etc. Through extensive screening and analyses, an antibody, H26L17, that specifically binds to NGF was finally obtained. The amino acid sequences of the heavy chain variable region and the light chain variable region of the antibody and the encoding DNA sequences thereof are set forth in SEQ ID NOs: 1-4.

2. Expression and Purification of Antibody

The encoding nucleotide sequence of the heavy chain variable region (set forth in SEQ ID NO: 1; the constant region is Ig gamma-1 chain C region, ACCESSION: P01857) and the encoding nucleotide sequence of the light chain variable region (set forth in SEQ ID NO: 3; the constant region is Ig lambda-2 chain C region; ACCESSION: P0CG05.1) of H26L17 were independently cloned into pUC57 simple vectors (provided by Genscript), and pUC57simple-H26L17H and pUC57simple-H26L17L plasmids were obtained respectively.

The plasmids pUC57simple-H26L17H and pUC57simple-H26L17L were digested (HindIII & EcoRI), and the nucleotide sequences of the heavy chain and light chain recovered by electrophoresis were independently subcloned into pcDNA3.1 vectors, and the recombinant plasmids were extracted to co-transfect 293F cells. After the transfected 293F cells were cultured for 7 days, the culture medium was centrifuged at high speed, and the obtained supernatant was concentrated and loaded onto a HiTrap MabSelect SuRe column. The protein was eluted in one step with the eluent to isolate the target sample. The antibody sample was stored in PBS buffer.

Figure 1:
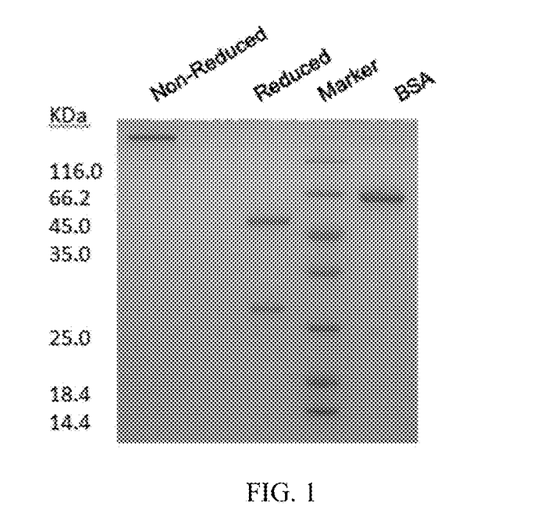
FIG. 1 shows the SDS-PAGE analysis results of the monoclonal antibody H26L17 against nerve growth factor of the present invention. The samples of the four lanes from left to right and respective loading amounts thereof are: antibody in non-reduced protein electrophoresis loading buffer, 1 μg; antibody in reduced protein electrophoresis loading buffer, 1 μg; protein molecular weight marker (Marker), 5 μL; bovine serum albumin (BSA), 1 μg.

The purified sample was added to both a reduced protein electrophoresis loading buffer and a non-reduced protein electrophoresis loading buffer, and then boiled. The processed samples were analyzed by SDS-PAGE electrophoresis. The electropherogram of H26L17 is shown in FIG. 1. The target protein sample in the reduced buffer is at 45 kD and 30 kD, and the target protein sample in the non-reduced buffer (single antibody) is at 150 kD.

The H26L17 prepared in this example was used in the following examples 2 to 4.

Example 2. Analysis of the Binding Activity of H26L17 to the Antigen Human β-NGF In this experiment, the ELISA method was used to determine the $EC_{50}$ (median effect concentration) of H26L17 binding to human β-NGF to investigate the binding specificity and affinity of the antibody to human β-NGF.

A microplate was coated with 50 L of 0.5 μg/mL human β-NGF in each well, and incubated overnight at 4° C. After the microplate was washed once and patted dry, each well was blocked with 300 L of 1% BSA solution (dissolved in PBS). The microplate was incubated at 37° C. for 2 h, and patted dry after being washed three times. The antibody was diluted to 1 μg/mL as the initial concentration, and a 1:3 gradient dilution was performed in the microplate to obtain a total of 7 concentrations, in addition to a blank control well. Duplicate wells were set for the above concentrations, with a final volume of 100 μL per well, and the microplate was incubated at 37° C. for 30 min. After the microplate was washed three times and patted dry, 50 μL of horseradish peroxidase-labeled goat anti-human IgG (H+L) secondary antibody working solution was added to each well, and the microplate was incubated at 37° C. for 30 min. After the microplate was washed four times and patted dry, 50 μL of TMB chromogenic solution was added to each well for color developing at room temperature for 5 min in the absence of light, then 50 μL of stop solution was added to each well to stop the color developing reaction. Immediately after the reaction was terminated, the microplate was placed in a microplate reader, and 450 nm light wavelength was selected to read the OD value of each well of the microplate. SoftMax Pro 6.2.1 software was used to analyze and process the data.

Figure 2:
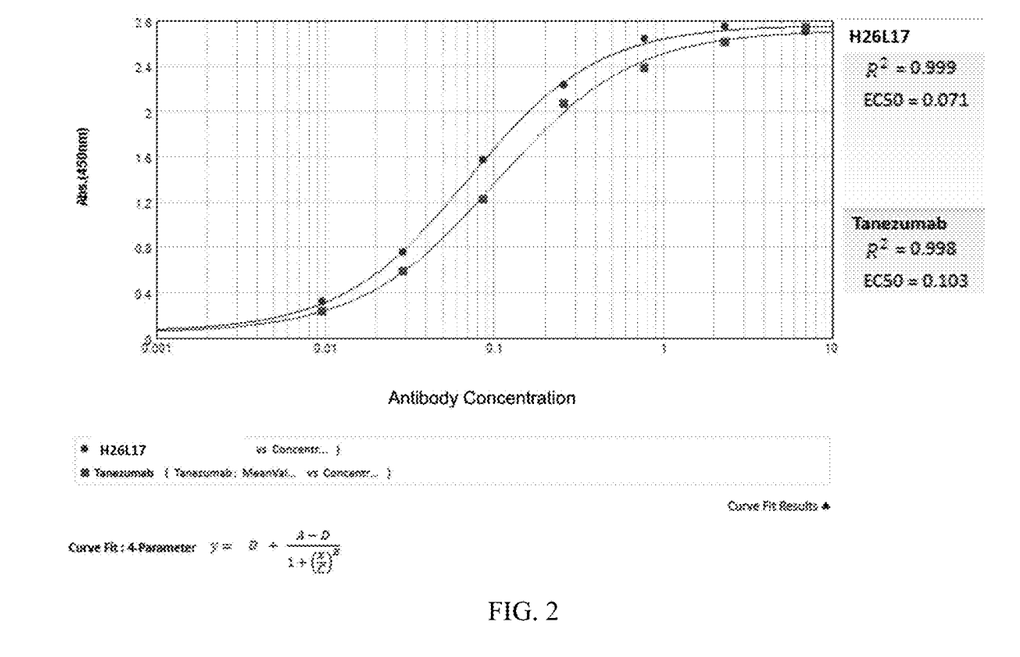
FIG. 2 shows the analysis results of the binding activity of H26L17 and Tanezumab to the antigen human R-NGF.

It can be seen from Table 2 and FIG. 2 that the 450 nm reading results show that H26L17 can effectively bind to human β-NGF, and the binding efficiency is dose-dependent. Taking the antibody concentration as the abscissa and the absorbance value as the ordinate, a 4-parameter fitting curve was plotted, resulting in a binding $EC_{50}$ of 0.071 nM, comparable to that of Tanezumab. See Table 2 for the analysis results of the binding activity of H26L17 and Tanezumab to human β-NGF. The results show that the binding of H26L 17 to the antigen human j-NGF is dose-dependent, with a binding $EC_{50}$ of 0.071 nM, comparable to Tanezumab.

TABLE 2

The analysis results of the binding activity of H26L17 and Tanezumab to the antigen human β-NGF

| Antibody dilution | Antigen-antibody binding OD (450 nm) value | | | |
|---|---|---|---|---|
| | H26L17 | | Tanezumab | |
| 1 μg/mL | 2.730 | 2.655 | 2.770 | 2.705 |
| 1:3 | 2.704 | 2.797 | 2.656 | 2.553 |
| 1:9 | 2.663 | 2.605 | 2.482 | 2.274 |
| 1:27 | 2.242 | 2.222 | 2.166 | 1.969 |
| 1:81 | 1.613 | 1.525 | 1.178 | 1.266 |
| 1:243 | 0.779 | 0.735 | 0.560 | 0.609 |
| 1:729 | 0.323 | 0.313 | 0.227 | 0.245 |
| 0 | 0.047 | 0.046 | 0.044 | 0.045 |
| $EC_{50}$ (nM) | 0.071 | | 0.103 | |

Example 3. Analysis of Cell Biological Activity of H26L17

Figure 3:
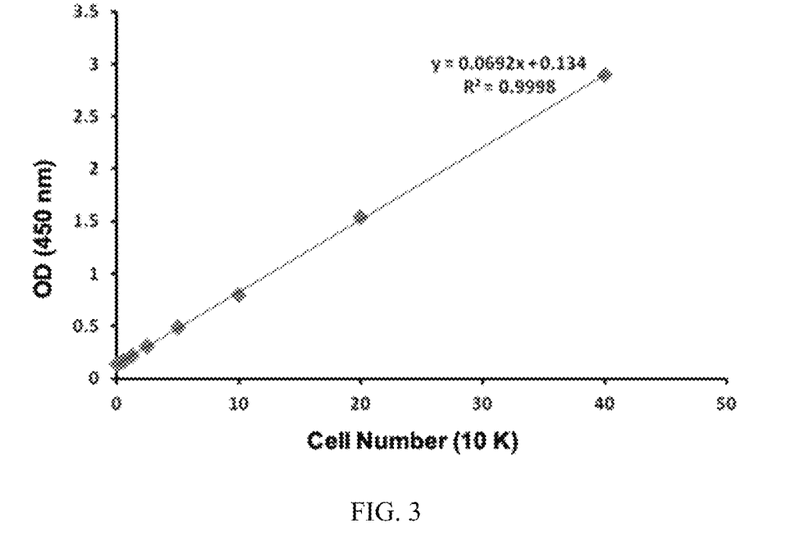
FIG. 3 shows the standard curve results for the analysis of H26L17 and Tanezumab inhibition on TF-1 cell proliferation by the CCK-8 method.
Figure 4:
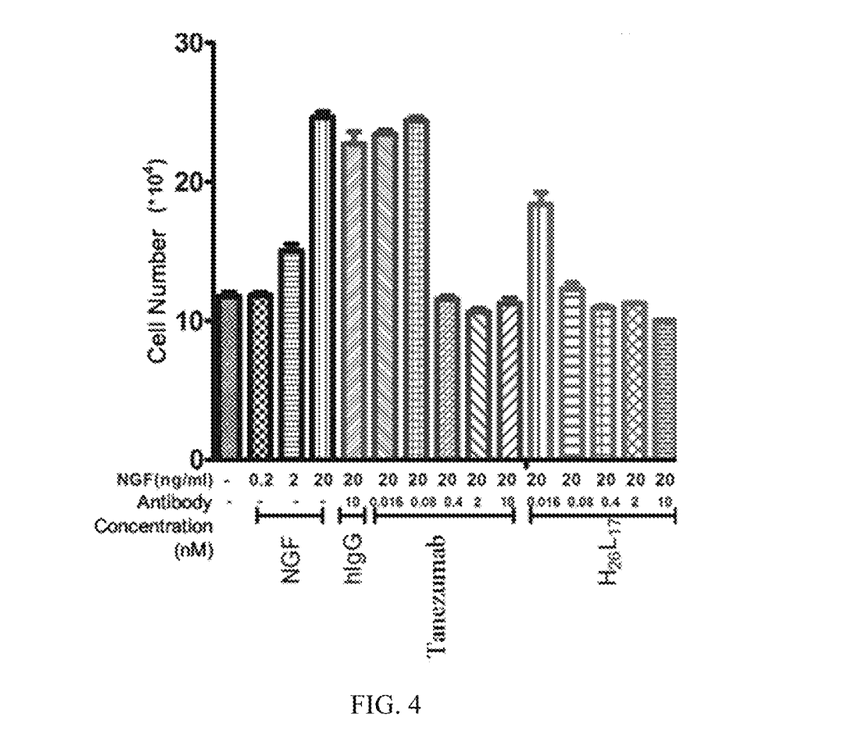
FIG. 4 shows the cell quantity after 72 h of inhibition of NGF-induced TF-1 cell proliferation by the monoclonal antibody H26L17 against nerve growth factor of the present invention.

1. Analysis of the Pharmacological Activity of H26L17 in Inhibiting NGF-Induced TF-1 Cell Proliferation In order to analyze the effect of H26L17 in inhibiting NGF-dependent TF-1 cell proliferation, antibodies, NGF and TF-1 cells of different concentrations were co-incubated and the cell proliferation was measured after 72 h of culturing. The specific procedures are as follows:

TF-1 cells were collected by centrifugation and counted, and 40,000 cells were seeded in each well of a 96-well plate. For administration, the control group was set with three NGF concentrations: 0.2, 2, and 20 ng/mL, and the antibody group was set with 20 ng/mL NGF; the antibody was set with five concentrations: 0.016 nM, 0.08 nM, 0.4 nM, 2 nM, and 10 nM. Before administering the NGF/antibody premix to cells, the antibody and NGF were pre-incubated at 37° C. for 30 min. In the experiment, an isotype control group was also included. After the cells were cultured for 72 h (pipetted and homogenized once every 24 h) post treatment, cell proliferation was measured according to the instructions of the CCK-8 test kit (100 μL of liquid was taken for analysis). The standard curve of cell proliferation is shown in FIG. 3. The analysis results of cell proliferation after 72 h of cell incubation are shown in FIG. 4. As seen in FIG. 4, H26L17 inhibits the stimulation effect of NGF on TF-1 cell proliferation in a dose-dependent manner. In particular, when the antibody concentration is lower than 0.08 nM, the H26L17 antibody is significantly better than the positive control antibody Tanezumab in inhibiting the effect of NGF on TF-1 cell proliferation.

2. $EC_{50}$ Value of H26L17 Neutralizing NGF in the Experiment of H26L17 Inhibiting NGF-Induced TF-1 Cell Proliferation To analyze the pharmacological activity of H26L17 in inhibiting NGF-induced TF-1 cell proliferation and calculate the $EC_{50}$ of H26L17 neutralizing NGF, antibodies, NGF and TF-1 cells of different concentrations were co-incubated and the cell proliferation was measured after 72 h of culturing. The specific procedures or methods are briefly described as follows:

TF-1 cells were collected by centrifugation and seeded in a 96-well plate with 40,000 cells per well. For administration, the control group was set with three NGF concentrations: 0.06 nM, 0.3 nM, and 1.5 nM. The final concentration of NGF in the NGF/antibody premix group was 1.5 nM, and the concentrations of antibodies were 0.0468 nM, 0.07 nM, 0.105 nM, 0.158 nM, 0.237 nM, 0.356 nM, 0.533 nM, and 0.8 nM, respectively. Before administering the NGF/antibody premix to cells, the antibody and NGF were pre-incubated at 37° C. for 30 min. In the experiment, an isotype antibody control group with a concentration of 1.5 nM was included. After the cells were cultured for 72 h (pipetted and homogenized once every 24 h) post treatment, cell proliferation was measured according to the instructions of the CCK-8 test kit (100 μL of liquid was taken for analysis).

Figure 5:
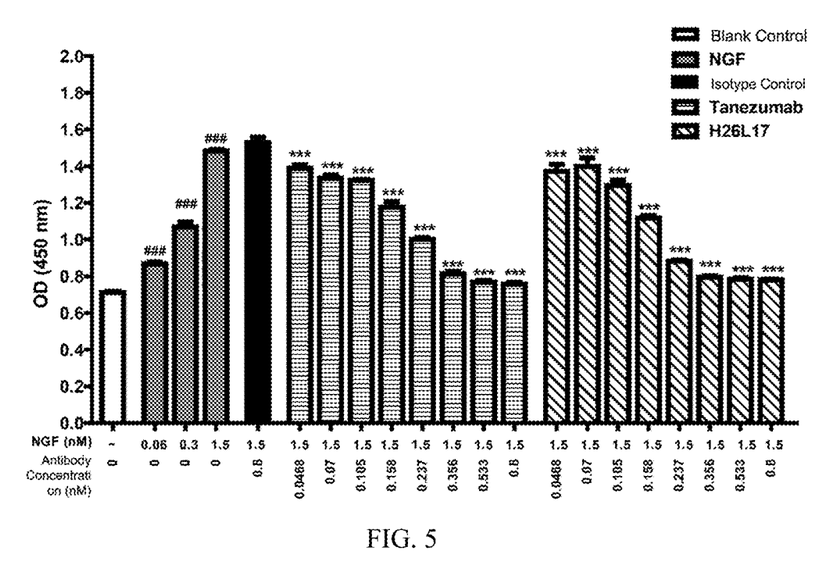
FIG. 5 shows the OD value of each group in measuring the inhibition of TF-1 cell proliferation by H26L17 and Tanezumab by the CCK-8 method.
Figure 6:
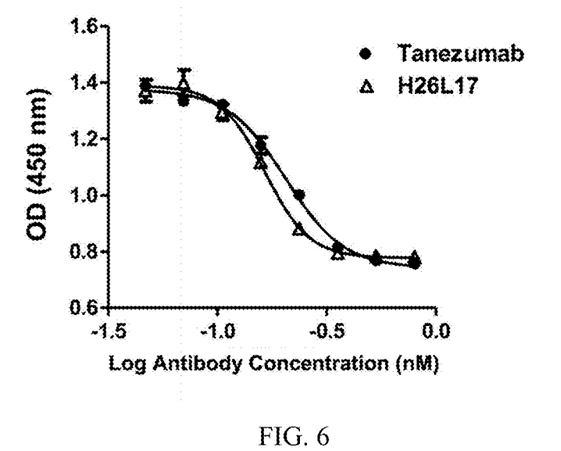
FIG. 6 shows the fitting curve of H26L17 inhibiting NGF-induced TF-1 cell proliferation. Taking the logarithm of antibody concentration (nM) as the x-axis and the OD 450 nm value as the y-axis, dose-effect curve fitting was performed to compare the $EC_{50}$ of different antibodies.

The OD values of each group measured in the CCK-8 experiment are shown in FIG. 5. Taking the logarithm of antibody concentration (nM) as the x-axis and the OD 450 nm value as the y-axis, the dose-effect curve fitting was performed to compare the $EC_{50}$ of different antibodies, and the fitting curve is shown in FIG. 6. H26L17 can inhibit the NGF-induced TF-1 cell proliferation in a dose-dependent manner, showing a neutralizing activity against NGF, and the activity is slightly better than that of the marketed drug Tanezumab for the same target. The neutralizing $EC_{50}$ to NGF of the two are 0.16 nM and 0.21 nM, respectively, and the H26L17 antibody is significantly better than the positive control antibody Tanezumab in inhibiting the effect of NGF on TF-1 cell proliferation.

Example 4. H26L17 can Improve the Walking Behavior of the Affected Limb and Alleviate the Weight Loss in the Knee Arthritis Pain Model of Lenti-IL-1β-NIH/3T3 Mice Patients with arthritis would experience lameness and other behavioral changes due to pain, as well as weight loss resulted from reduced food intake due to bad emotions induced by the pain. In order to measure the alleviation of anti-NGF antibody to knee arthritis pain response, a mouse model of knee arthritis pain induced by Lenti-IL-1β-NIH/3T3 was established, and the drug efficacy was evaluated by behavioral improvement of mice. In this model, Lenti-IL-1β-NIH/3T3 cells overexpressed IL-1β in the joint cavity of mice, which in turn induced joint inflammation and pain at the injection site. In this experiment, 60 C57BL/6 mice were divided into 6 groups according to body weight, namely normal group (saline, S.C.), model group (anti-HEL, 20 mg/kg, S.C.), Tanezumab group (Tanezumab, 20 mg/kg, S.C.) and H26L17 antibody low-dose group (H26L17, 0.2 mg/kg, S.C.), medium-dose group (H26L17, 2 mg/kg, S.C.), and high-dose group (H26L17, 20 mg/kg, S.C.), 10 animals per group. The day of grouping was recorded as day 0 (D0). After grouping, the mice were weighed, and the corresponding drugs were injected subcutaneously according to the mouse body weight at an administration volume of 10 mL/kg. The drugs were administered three times in total, and were administered subcutaneously on D0, D3, and D6 respectively after grouping. After administration on the day of grouping, 10 C57BL/6 mice in the normal group were inoculated with NIH/3T3 cell suspension (50,000 cells/mouse) in the knee joint cavity, and the other 50 C57BL/6 mice in the remaining groups were inoculated with Lenti-IL-1β-NIH/3T3 cell suspension (50,000 cells/mouse) in the knee joint cavity. Then behavioral scoring of mice was conducted on D3, D5 and D11 after administration on the day of grouping.

Figure 7:
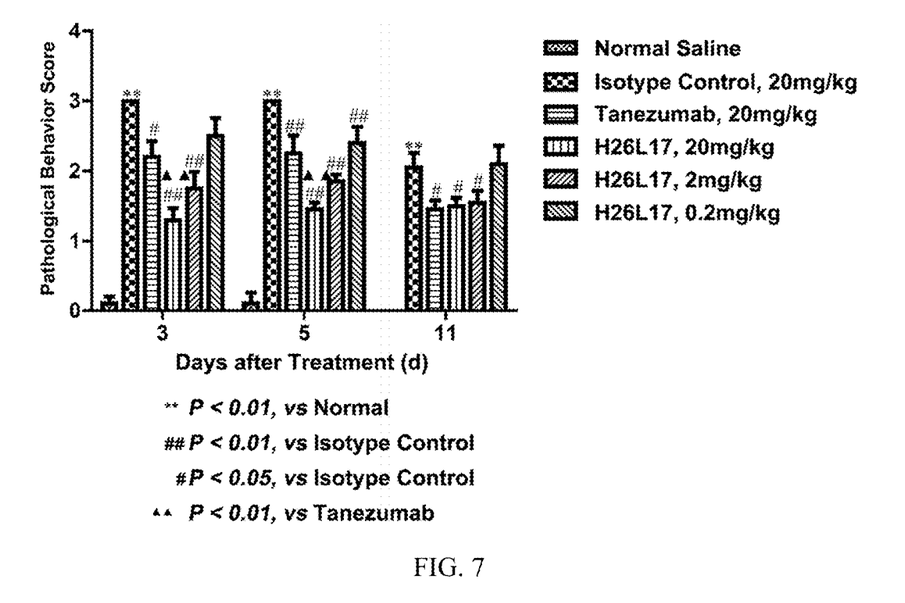
FIG. 7 shows the effect of H26L17 on the walking behavior of the affected limb caused by pain in the knee arthritis pain model of Lenti-IL-1β-NIH/3T3 mice.
Figure 8:
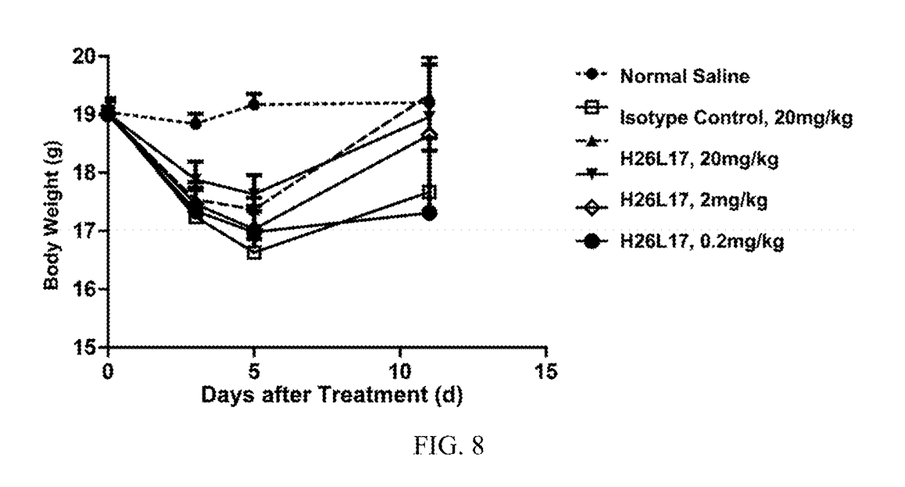
FIG. 8 shows the effect of H26L17 on the weight of mice in the knee arthritis pain model of Lenti-IL-1β-NIH/3T3 mice.

The results of the effect of anti-NGF antibody on the knee joint pain response in mice are shown in FIG. 7. Compared with the positive control antibody Tanezumab (20 mg/kg, S.C.), the H26L17 high-dose group (20 mg/kg, S.C.) reduces pain response significantly; compared with the positive control antibody Tanezumab (20 mg/kg, S.C.), the H26L17 antibody low-dose group (0.2 mg/kg, S.C.) and the H26L17 medium-dose group (2 mg/kg, S.C.) have equivalent effect in reducing pain in mice. The results of anti-NGF antibody alleviating the weight loss of mice in the mouse knee arthritis pain model are shown in FIG. 8. The H26L17 antibody medium and high dose groups have equivalent effect as the positive control antibody Tanezumab in alleviating the weight loss of mice in the mouse knee arthritis pain model, more significant than the isotype control anti-HEL.

The preferred embodiments of the present invention have been described above in detail, but the present invention is not limited to the embodiments. Those skilled in the art can make various equivalent modifications or replacements without violating the spirit of the present invention. These equivalent modifications or replacements are included in the scope defined by the claims of the present application.

What is claimed is:

1. A monoclonal antibody, or an antigen binding fragment thereof, wherein the monoclonal antibody or the antigen binding fragment thereof binds to nerve growth factor (NGF) protein, comprising:
   a) a heavy chain variable region (VH) comprising complementarity determining regions (CDRs) having the amino acid sequences set forth in SEQ ID NOs: 5-7; and
   b) a light chain variable region (VL) comprising CDRs having the amino acid sequences set forth in SEQ ID NOs: 8-10.

2. The monoclonal antibody or antigen binding fragment thereof of claim 1, wherein
   the VH comprises the amino acid sequence set forth in SEQ ID NO: 2, and
   the VL comprises the amino acid sequence set forth in SEQ ID NO: 4.

3. The monoclonal antibody or antigen binding fragment thereof of claim 1, wherein the monoclonal antibody or antigen binding fragment thereof is selected from an Fab, an Fab', an F(ab')2, an Fd, an Fv, a dAb, a single chain antibody, a humanized antibody, a chimeric antibody, and a diabody.

4. The monoclonal antibody or antigen binding fragment thereof of claim 1, wherein the monoclonal antibody or antigen binding fragment thereof binds to NGF protein with an $EC_{50}$ of less than about 100 nM.

5. The monoclonal antibody or antigen binding fragment thereof of claim 1, wherein the monoclonal antibody or antigen binding fragment thereof comprises non-CDR regions derived from species other than mouse.

6. A nucleic acid molecule, comprising a nucleic acid sequence encoding the VH and a nucleic acid sequence encoding the VL of the monoclonal antibody or antigen binding fragment thereof of claim 1.

7. The nucleic acid molecule of claim 6, wherein
   the nucleic acid sequence encoding the VH comprises the nucleic acid sequence set forth in SEQ ID NO: 1, and
   the nucleic acid sequence encoding the VL comprises the nucleic acid sequence set forth in SEQ ID NO: 3.

8. A vector, comprising the nucleic acid molecule of claim 6.

9. A host cell, comprising the vector of claim 8.

10. A conjugate comprising the monoclonal antibody or antigen binding fragment thereof of claim 1 and a conjugated portion comprising a detectable label.

11. The conjugate of claim 10, wherein the detectable label comprises a radioisotope, a luminescent substance, a colored substance, an enzyme or any combination thereof.

12. A method of detecting the presence or amount of NGF protein in a biological sample, the method comprising contacting the biological sample with the conjugate of claim 10.

13. A kit comprising the monoclonal antibody or antigen binding fragment thereof of claim 1.

14. A pharmaceutical composition comprising the monoclonal antibody or antigen binding fragment thereof of claim 1 and at least one pharmaceutically acceptable carrier or excipient.

15. A method of treating pain in a subject in need thereof, comprising administering to the subject at least one effective amount of the monoclonal antibody or antigen binding fragment thereof of claim 1.

16. The method of claim 15, wherein the pain is neuropathic pain.

17. The method of claim 15, wherein the pain is chronic pain.

18. The method of claim 15, wherein the pain is inflammatory pain.

19. A method of detecting the presence or amount of NGF protein in a biological sample, comprising contacting the biological sample with the monoclonal antibody or antigen binding fragment thereof of claim 1.

20. A method of inhibiting the proliferation of NGF-dependent TF-1 cells, comprising contact the NGF-dependent TF-1 cells with the monoclonal antibody or antigen binding fragment thereof of claim 1.

21. The method of claim 15, wherein the pain is cancer pain.

* * * * *

UNITED STATES PATENT AND TRADEMARK OFFICE
CERTIFICATE OF CORRECTION

| | |
|---|---|
| PATENT NO. | : 11,680,095 B2 |
| APPLICATION NO. | : 17/048442 |
| DATED | : June 20, 2023 |
| INVENTOR(S) | : Zhongmin Maxwell Wang et al. |

It is certified that error appears in the above-identified patent and that said Letters Patent is hereby corrected as shown below:

On the Title Page

"(30) Foreign Application Priority Data
Apr. 17, 2018 (CN) ...................... 201810344670.3
Nov. 7, 2019 (CN) ...................... 201811320006.1"
Should read:
--(30) Foreign Application Priority Data
Apr. 17, 2018 (CN) ...................... 201810344670.3
Nov. 7, 2018 (CN) ...................... 201811320006.1--

Signed and Sealed this
Fifteenth Day of August, 2023

Katherine Kelly Vidal
*Director of the United States Patent and Trademark Office*